United States Patent
Panzini et al.

(10) Patent No.: US 9,808,403 B2
(45) Date of Patent: Nov. 7, 2017

(54) METHOD AND APPARATUS FOR MEDICATION STORAGE AND DELIVERY

(71) Applicants: Philippe Panzini, Westmount (CA); Hugo Tetreault, Montreal (CA)

(72) Inventors: Philippe Panzini, Westmount (CA); Hugo Tetreault, Montreal (CA)

(73) Assignee: Wulou Labs Inc., Wilmington, DE (US)

( * ) Notice: Subject to any disclaimer, the term of this patent is extended or adjusted under 35 U.S.C. 154(b) by 0 days.

(21) Appl. No.: 14/754,767

(22) Filed: Jun. 30, 2015

(65) Prior Publication Data
US 2016/0015602 A1 Jan. 21, 2016

Related U.S. Application Data

(60) Provisional application No. 62/019,425, filed on Jul. 1, 2014.

(51) Int. Cl.
| G06F 19/00 | (2011.01) |
| A61J 7/04 | (2006.01) |
| G01G 19/52 | (2006.01) |
| G01G 17/00 | (2006.01) |
| G01G 19/42 | (2006.01) |

(52) U.S. Cl.
CPC ........... *A61J 7/0481* (2013.01); *A61J 7/0454* (2015.05); *G01G 17/00* (2013.01); *G01G 19/52* (2013.01); *G06F 19/3456* (2013.01); *G06F 19/3462* (2013.01); *A61J 2200/74* (2013.01); *A61J 2205/60* (2013.01); *G01G 19/42* (2013.01); *G06F 19/30* (2013.01); *G06F 19/345* (2013.01); *G06F 19/3475* (2013.01); *G06F 19/3487* (2013.01)

(58) Field of Classification Search
CPC ............... G06F 19/345; G06F 19/3475; G06F 19/3487; G06F 19/30; G06F 19/3462; A61J 2200/74; A61J 2200/70; A61J 2205/60; A61J 7/04; A61J 7/0427; A61J 7/0454; A61J 7/0481; G01G 17/00; G01G 19/42; G01G 19/52; G08B 5/36
USPC .......................... 206/534; 340/666; 345/205
See application file for complete search history.

(56) References Cited

U.S. PATENT DOCUMENTS

| 6,294,999 | B1* | 9/2001 | Yarin | A61J 7/0481 340/573.1 |
| 2003/0214129 | A1* | 11/2003 | Adler | A61J 7/04 283/81 |
| 2007/0272583 | A1* | 11/2007 | Kulkarni | G06F 19/3462 206/528 |
| 2012/0101630 | A1* | 4/2012 | Daya | G06F 19/325 700/231 |
| 2013/0195326 | A1* | 8/2013 | Bear | A61J 7/0076 382/128 |
| 2013/0256331 | A1* | 10/2013 | Giraud | A61J 7/0409 221/1 |

* cited by examiner

*Primary Examiner* — Benyam Haile
(74) *Attorney, Agent, or Firm* — Robert A. Diaz

(57) ABSTRACT

An intelligent pill box device comprising: a base and a display panel. The base includes a plurality of cylindrical shaped receptacles for storing medication bottles wherein each receptacle includes a radio frequency identification reader, a faraday cage, and a load cell at the bottom of the receptacle to measure the weight of the contents of the receptacle.

11 Claims, 16 Drawing Sheets

METHOD AND APPARATUS FOR MEDICATION STORAGE AND DELIVERY

FIELD

This patent application relates to a method for providing a medication notification to a patient.

BACKGROUND

In the United States and around the world there are a large number of people that are living longer than previous generations. This is leading to a growing number of aging citizens that require medication. Most require multiple medications taken at different intervals. Some elderly people find it difficult to remember to take their medication or are sometimes confused by prescription directions.

Various tools exist to help people cope with the burden of taking medication. Existing devices provide audible beeps or messages to alert an individual that it is time to take their medication. Some of these devices can be programmed with complex scheduling information. Some devices are meant for a single pill bottle while others have multiple compartments for different medication and can be programmed for a plurality of medication and scheduling.

The existing technology has several shortcomings: first, existing devices require programming by the user, which is often problematic since many are elderly; second, the devices are not aware of the specific medication in a bottle unless the user programs this information into the device; third, existing devices have no way of measuring the amount of pills within a bottle in order to verify compliance with a prescription.

Therefore, there is a need for a method and apparatus that can interact directly with a pill bottle to extract information regarding a prescription associated with the pill bottle, and that can use said information to create a schedule for taking those pills. There is also a need for a device that can monitor the removal of every pill from said pill bottle to track compliance with said prescription. There is also a need for a device that can determine negative drug interactions between multiple medications and generate alerts for a user.

SUMMARY

An intelligent pill box device, comprising: a base and a display panel; said base including a plurality of cylindrical shaped receptacles for storing medication bottles, each receptacle including a radio frequency identification reader, and each receptacle surrounded by a faraday cage, and each receptacle containing a load cell at the bottom of the receptacle to measure the weight of the contents of the receptacle; and said base including a processing device and a memory, said processing device executing at least: instructions relating to weighing medication in a receptacle, and instructions relating to using said reader to extract information from the label on a medication bottle within a receptacle, and instructions relating to using at least said weight and said extracted information to determine a schedule for taking said medication and notifying a user when it is time to take said medication, and monitoring compliance with said schedule; said display panel attached to the base with a hinge, and said display panel including a flat screen display to display information to a user.

A medication assistance method, comprising: using a radio frequency identification reader to read information from a radio frequency identification tag on a bottle containing pills placed in a receptacle; and using said information to determine a schedule for taking the pills within said bottle; and using a weight measuring means to weigh said bottle and said pills; and using a calibration process and said measuring means to determine the average weight of individual pills within said bottle; and alerting a user to take one or more of said pills according to said schedule; and monitoring the weight of said bottle with said weight measuring means; and determining whether said user took said pills according to said schedule.

BRIEF DESCRIPTION OF THE DRAWINGS

A full understanding of the invention can be gained from the following description of certain embodiments of the invention when read in conjunction with the accompanying drawings in which.

DETAILED DESCRIPTION

In the following description the term "module" refers broadly to software, hardware, or firmware (or any combination thereof) components. Modules are typically functional components that can generate useful data or other output using specified input(s). A module may or may not be self-contained. An application program (also called an "application") may include one or more modules, or a module can include one or more application programs.

Figure 1:
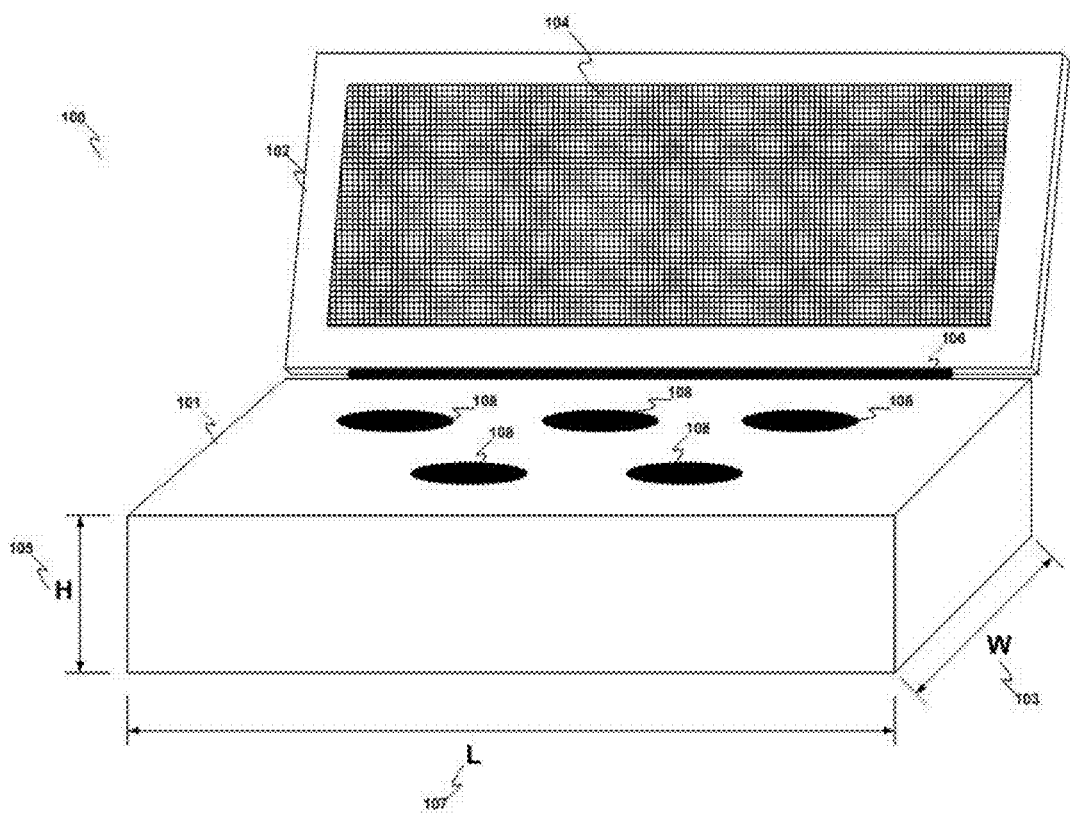
FIG. 1 is a schematic illustrating an isometric view of an intelligent pill box, in accordance with one embodiment.

In accordance with many embodiments, and illustrated in FIG. 1 is an intelligent pill box. FIG. 1 provides an isometric view of the intelligent pill box. The said intelligent pill box [100] includes a base [101] and a hinged panel [102]. The hinged panel contains an electronic display [104]. The display [104] can be any type of flat screen display including liquid crystal display (LCD), Light emitting diode (LED) display, organic light emitting diode (OLED) display, and the like. The display [104] can comprise a touch screen display. The hinged panel [102] swivels about a hinge [106] that connects the hinged panel [102] to the base [101]. The base includes a plurality of receptacles [108]. The receptacles are cylindrically shaped cavities with openings on the top surface of the base. The receptacles have circular cross section.

Figure 2:
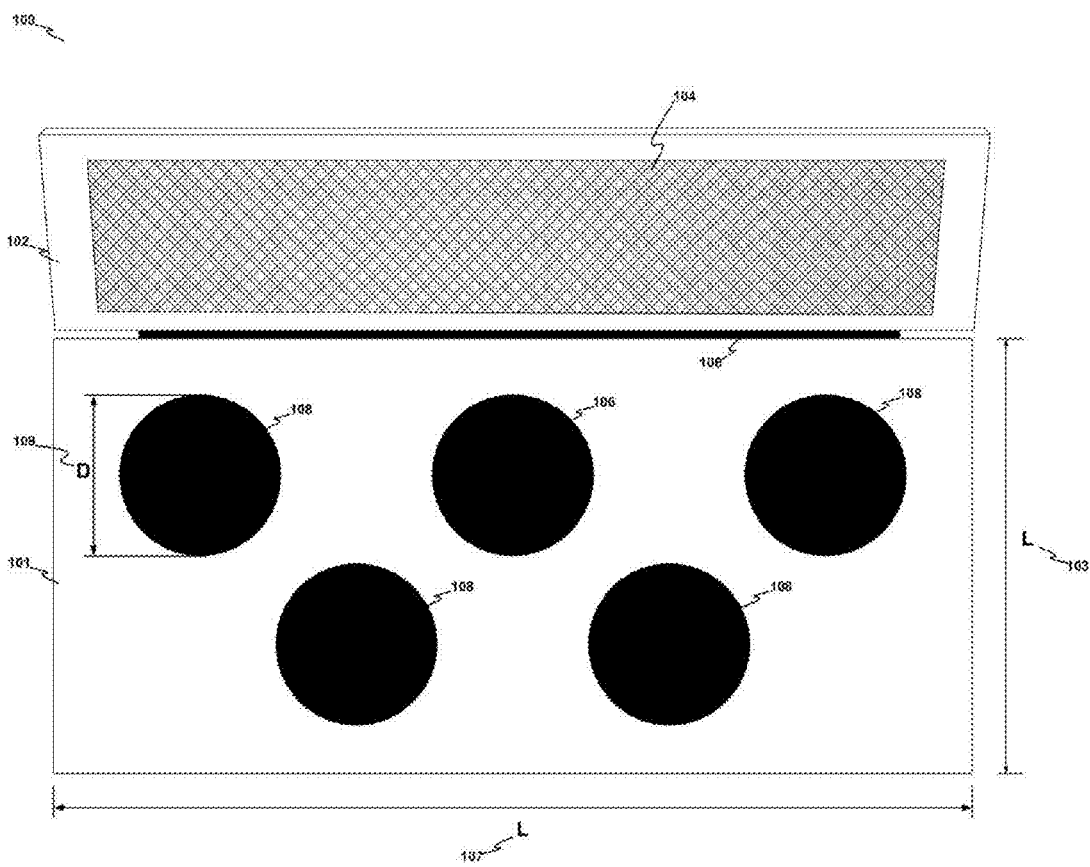
FIG. 2 is a schematic illustrating a top view of an intelligent pill box, in accordance with one embodiment.

In accordance with one embodiment and illustrated in FIG. 2 is the top view of an intelligent pill box [100]. The intelligent pill box base [101] contains 5 receptacles wherein each receptacle has the same diameter denoted by the letter D [109]. The base [101] can have more than 5 receptacles or it can have fewer than 5 receptacles. The diameter D [109] of the receptacles is about 2 inches. The diameter D [109] can be larger or smaller than 2 inches in order to accommodate larger or smaller sized pill bottles. The length [107] of the base is denoted by L in FIG. 1 and FIG. 2 and is about 12 inches. The length [107] can be longer than 12 inches or shorter than 12 inches in order to accommodate a different number of receptacles or a different sized display. The width [103] is denoted by the letter W in FIG. 1 and FIG. 2 and is about 5.5 inches. The height [105] of the base is denoted by the letter H in FIG. 1 and FIG. 2 and is about 3.5 inches. While FIG. 1 and FIG. 2 illustrate a base with receptacles of identical size, the size of each receptacle can be different without departing from the scope of this disclosure. For example, a base could contain 6 receptacles wherein three of said receptacles have a diameter D of 2 inches and the other three receptacles have a diameter of 3 inches. A receptacle with a large diameter can be used to hold large pill bottles and small pill bottles.

In accordance with an embodiment the hinged panel [102] is detachable from the base [101]. This allows for a user to remove the panel [102] to more easily read and interact with the display [104]. The detachable panel includes a wireless device that can communicate with the base wirelessly to receive display information from said base and to transmit to said base user input information. The user input information is received by the detached panel [102] via physical keys on the panel and via a touch screen.

Figure 3:
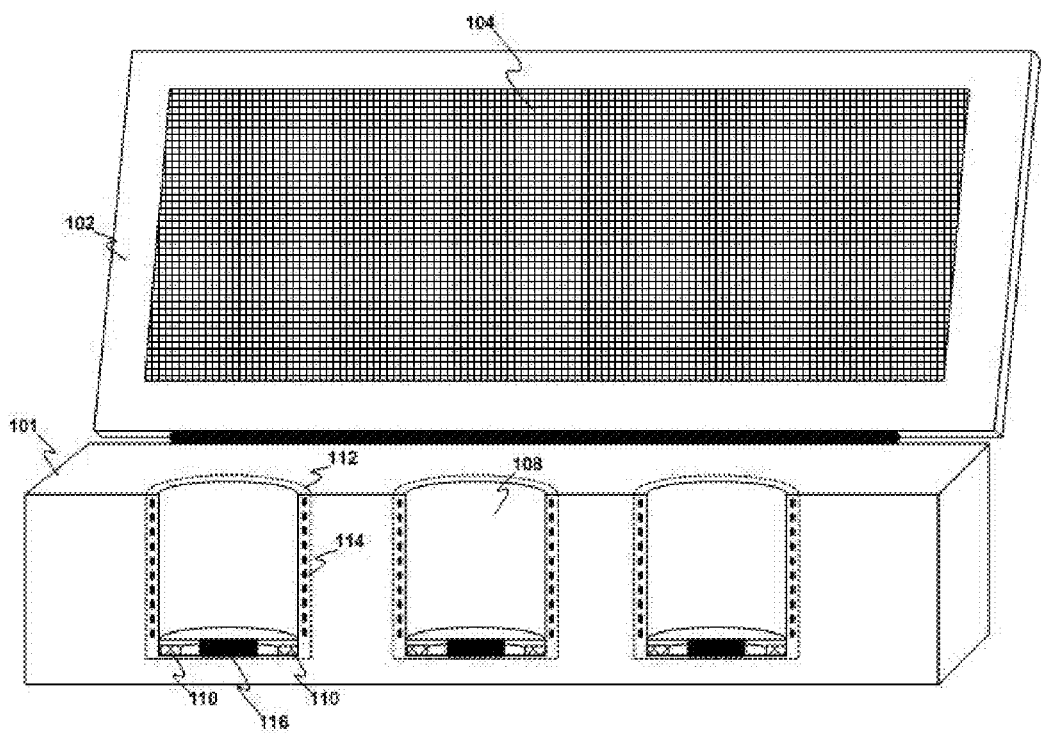
FIG. 3 is a schematic illustrating an isometric cross-sectional view of an intelligent pill box, in accordance with one embodiment.

In accordance with an embodiment FIG. 3 is an illustration of a cross sectional isometric view of an intelligent pill box. The cross section is taken across the length of the base [101] so that three receptacles are cut in half. A receptacle comprises a cavity [108], a load cell [116], a radio frequency identification (RFID) reader [114], a Faraday cage [112] and one or more lights [110]. The depth of each cavity in FIG. 3 is about 2 inches. The Faraday cage [112] surrounds the cavity [108] and the RFID reader [114]. The said Faraday cage helps to block an RFID signal from any adjacent receptacles. The Faraday cage [112] is known to those familiar in the art and can consist of a mesh of metal wires or a metal cage. The load cell [116] is a transducer that converts the force from the weight of a pill bottle into an electrical signal. The load cell [116] is at the base of the cavity and is used to monitor the weight of a pill bottle placed in a receptacle. The receptacles in FIG. 3 are cylindrical in shape and all have the same diameter and depth. However, the diameter of each receptacle can be different and the depth of each receptacle can be different.

Figure 4:
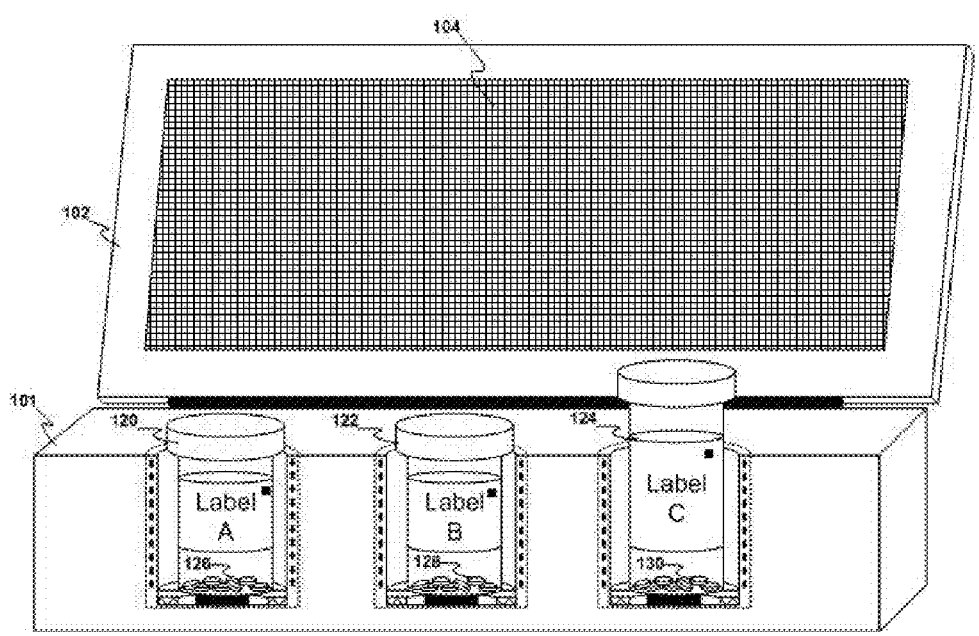
FIG. 4 is a schematic illustrating an isometric cross-sectional view of an intelligent pill box containing pill bottles, in accordance with one embodiment.

In accordance with an embodiment and illustrated in FIG. 4 is a cross sectional isometric view of an intelligent pill box containing three pill bottles. A first receptacle contains a small pill bottle [120] with a first set of pills [126]. The small pill bottle [120] rests on the load cell at the bottom of the receptacle. The load cell at the bottom of the receptacle measures the weight of the small pill bottle [120] and communicates this weight data with at least one computer processor that has memory. The said processor is within the base and executes instructions stored in memory in order to monitor the weight of the said pill bottle over time. Said weight monitoring is used to determine the number of pills taken out of said pill bottle and the time each pill is taken. The said monitoring can be done continuously, at intervals and intermittently. A second receptacle contains a small pill bottle [122] with a second set of pills [128], and a third receptacle contains a larger pill bottle [124] with a third set of pills [130].

Figure 5:
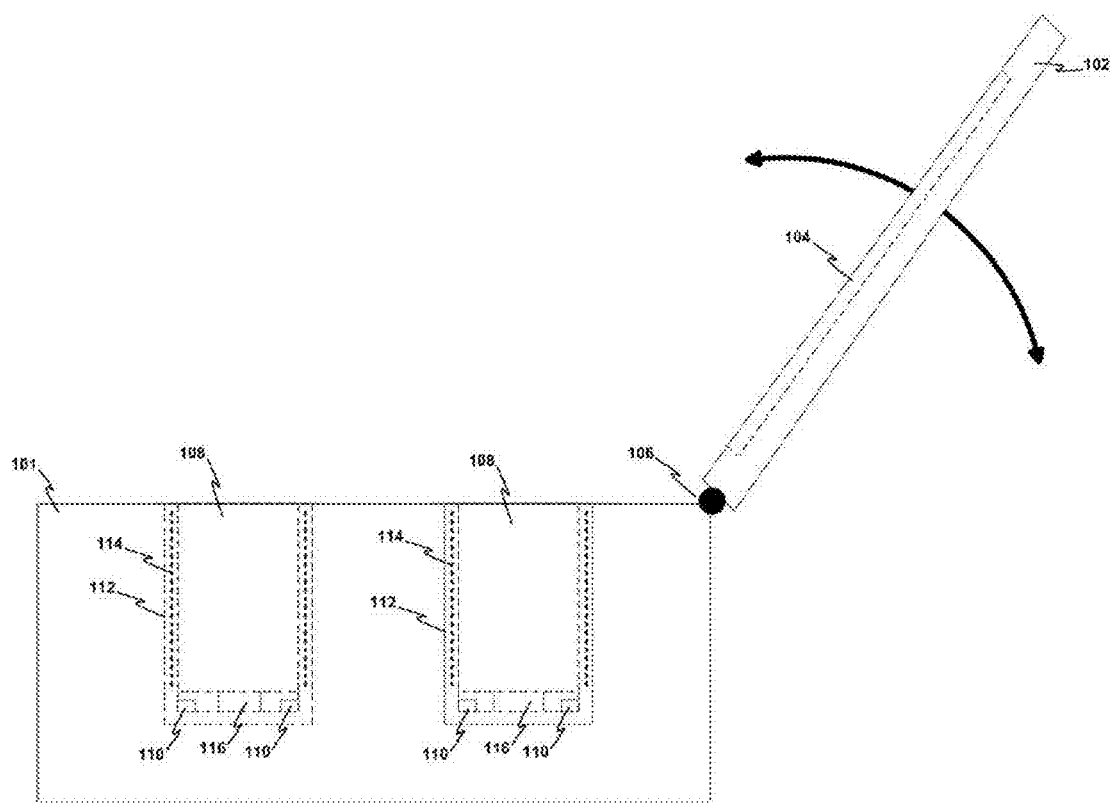
FIG. 5 is a schematic illustrating a cross-sectional side view of an intelligent pill box, in accordance with one embodiment.

In accordance with an embodiment and illustrated in FIG. 5 is a lateral cross sectional view of an intelligent pill box. The base [101] is connected to the hinged panel [102] with a hinge [106]. The hinge allows the panel to swivel.

Figure 6:
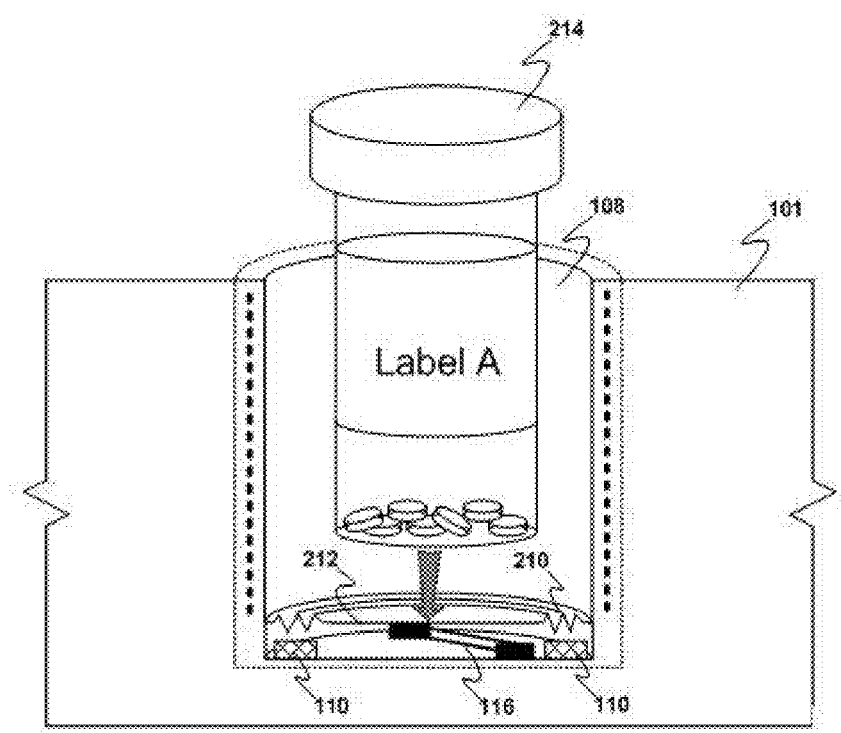
FIG. 6 is a schematic illustrating a cross-sectional view of a receptacle, in accordance with one embodiment.

In accordance with an embodiment and illustrated in FIG. 6 is a cross sectional view of a receptacle. The receptacle has a floating base plate [212] wherein the base plate [212] is connected to the receptacle walls [113] with a flexible ring shaped connector [210]. The flexible connector [210] in FIG. 6 has an accordion shape, but it can have other shapes including being flat. The flexible connector [210] can be made from a different material than the base plate [212]. For example the flexible connector [210] could be made from a very flexible plastic or other flexible material while the base plate [212] could be made of a harder plastic or other hard material. The flexible connector [210] allows the base plate to move in a vertical direction; for example a pill bottle placed on top of the base plate will push the base plate down and similarly the base plate will move upward when the bottle is removed. The bottom side of the base plate [212] is connected to the top part of a load cell [116] and the bottom of the load cell is connected to the pill box base [101]. The flexibility of the flexible connector [210] allows the base plate [212] to be pushed down into the load cell when a pill bottle [214] is placed in the receptacle. The downward pressure from the weight of the pill bottle compresses the load cell and allows it to measure the weight of the pill bottle. The output of the load cell is connected to a processor and a memory and the weight of the pill bottle is monitored and recorded by the processor and memory.

Figure 7:
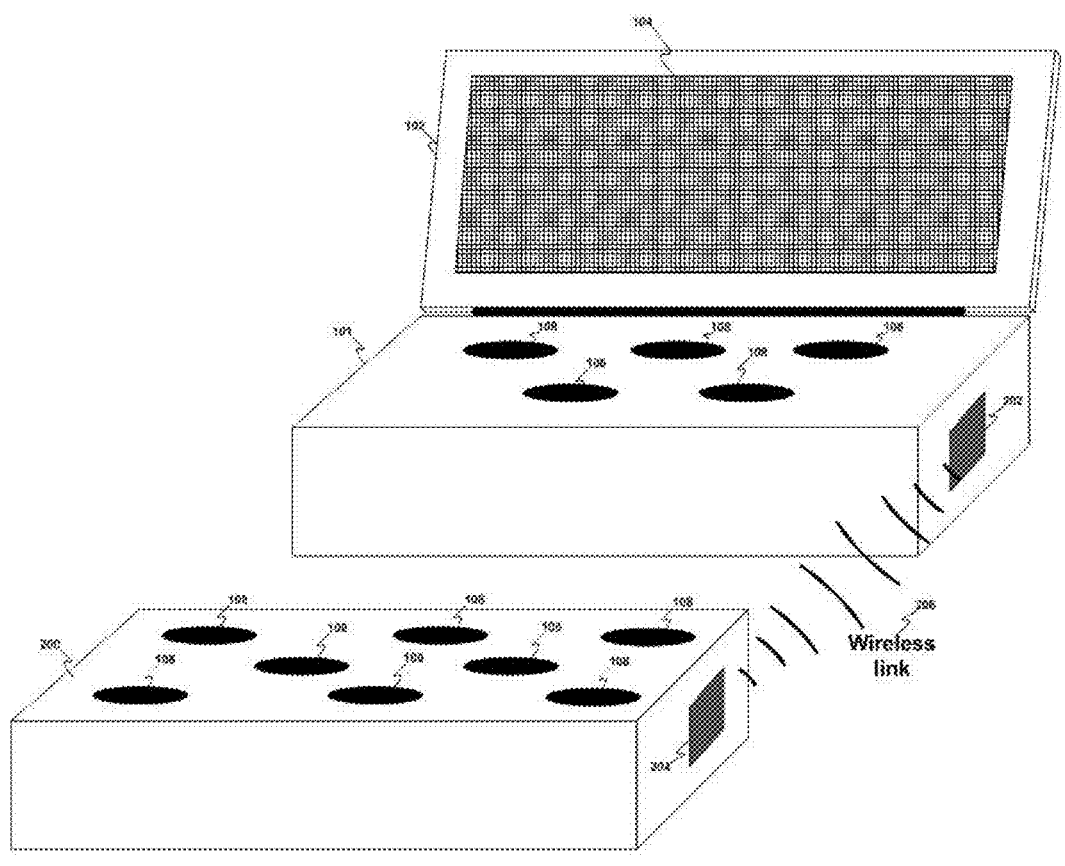
FIG. 7 is a schematic illustrating an intelligent pill box communicating with an additional intelligent pill box base, in accordance with one embodiment.

In another embodiment illustrated in FIG. 7, there is a second pill box base [200] with additional receptacles [108]. The said second pill box base [200] can work as an extension to the first pill box base [101]. The second pill box base [200] provides a user with more receptacles to hold pill bottles. This is useful for people who take more medication than can fit in the first pill box base. The second pill box base shown in FIG. 7 contains 8 receptacles. The said second pill box base does not have a panel with a display screen. The second pill box base [200] communicates with the first pill box base [101] via a wireless connection [206]. The wireless connection can use any wireless technology including Bluetooth, WiFi and NFC (Near Field Communication). The second pill box base [200] has at least one wireless communication device [204] and the first pill box base [101] has at least one wireless communication device [202]. In an alternate embodiment the said first pill box base [101] and the second pill box base [200] communicate via a wire or cable. When a user has a first pill box base [101] and a second pill box base [200] the user can place a pill bottle in any receptacle on either base. The two bases communicate with each other and work together such that all receptacles are equal. A notification in the display [104] that refers to a receptacle will indicate the location of said receptacle. The notification can be in the form of a text message such as 'Take medicine XYZ from receptacle 5 in base 1.' And the notification can be in a visual form on the display [104] showing visual representations of the two bases. For example FIG. 7 shows a visual representation of the first base [250] and the second base [252] on the display [104] along with a visual message [254] showing the user the correct medicine to take. In this example the display [104] shows the medication bottle [256] in the image of the second base [252] that corresponds to the actual bottle [258] in the same position within the actual second base [200].

Figure 8:
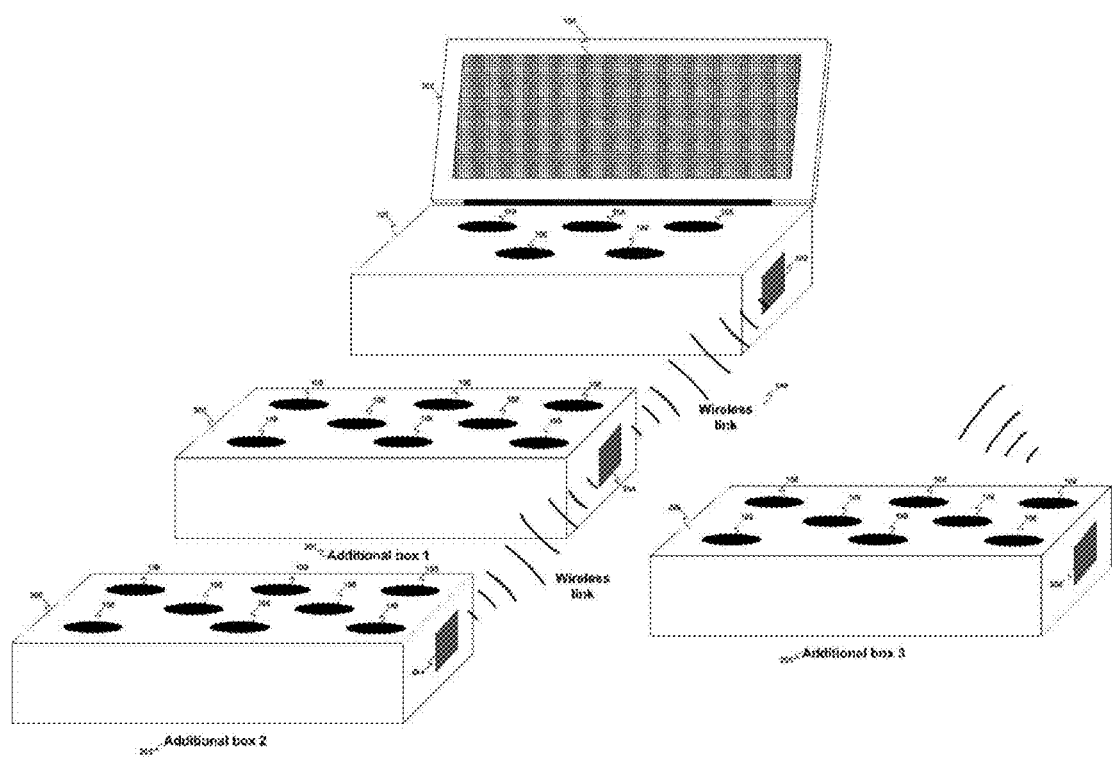
FIG. 8 is a schematic illustrating an intelligent pill box communicating with a plurality of intelligent pill box bases, in accordance with one embodiment.

In accordance with an embodiment and illustrated in FIG. 8 there are a plurality of pill box bases. The pill box bases are connected in a wireless network with each other. FIG. 8 shows 3 extra pill box bases, however there can be any number of additional pill box bases. An intelligent pill box base can communicate with any other pill box base via said network. For example, FIG. 8 shows that the second pill box base [200] has a wireless link [206] with the first pill box base [101] while the third pill box base [201] has a wireless link [220] with the second pill box base [200]. Regardless of the communication path between the first pill box base and an additional pill box base, the first pill box base determines the scheduling for taking the medication and communicates with the additional pill boxes to make the additional pill box do one or more of the following: turn on a light in a receptacle at the appropriate time, sound an audible alarm at the correct time, provide a weight reading from a receptacle load cell.

Figure 9:
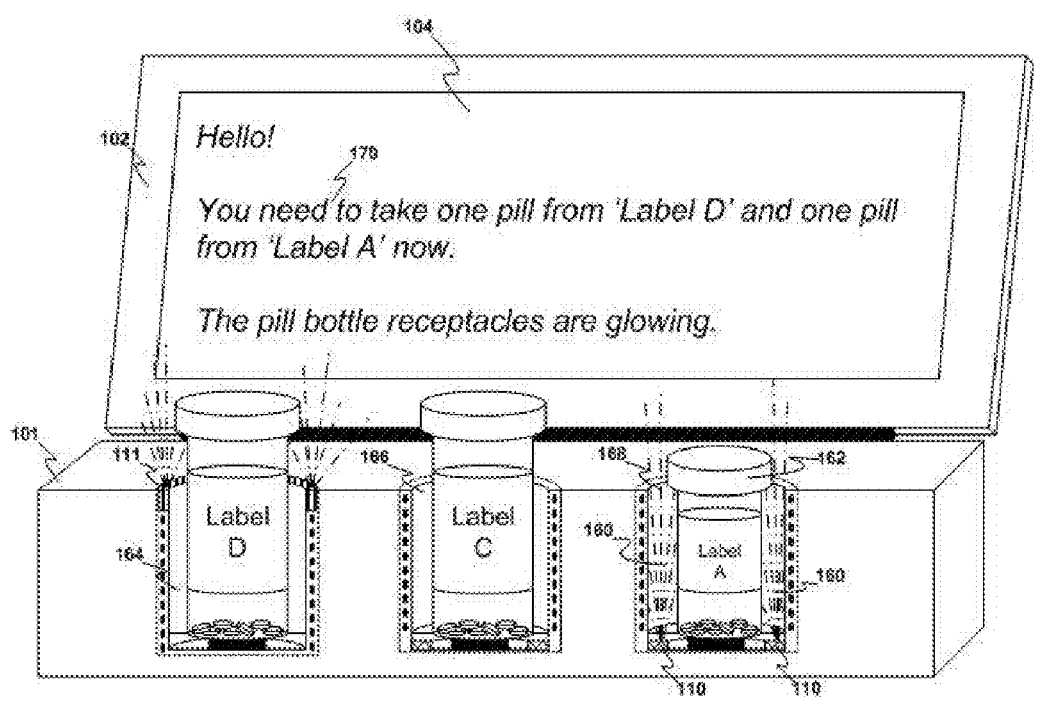
FIG. 9 is a schematic illustrating a cross sectional isometric view of an intelligent pill box with a display panel and lights, in accordance with an embodiment.

In accordance with an embodiment and illustrated in FIG. 9 is a cross-sectional isometric view of an intelligent pill box with lights in the receptacles. In one embodiment one or more lights [110] are placed at the bottom of a receptacle [168] and shine light [160] up through the receptacle around and through a pill bottle [162]. In another embodiment one or more lights [111] are placed at the top of a receptacle [164]. The said lights can be any form of compact light including a light emitting diode (LED) and organic light emitting diode (OLED). A light in a receptacle is connected at least to a patient alarm system so that it can visually alert users to a specific receptacle when it is time to take a specific medication, or if a medication is nearing an expiry date, or for any other reason an alarm or notification is created. As shown in FIG. 9 the display [104] is synchronized with the light in the receptacle so that a receptacle is highlighted by a light when it is mentioned on the display [104]. In the example shown the text in the display informs the user to take one pill from a first bottle [166] in a first receptacle [164] with the label 'Label D' at the same time as the light [111] around the receptacle is on. Similarly, the text in the display also informs the user to take one pill from a second bottle [162] in a second receptacle [168] with the label 'Label A' at the same time as light [110] in the receptacle is on. Synchronizing the light with the display helps the user to take pills from the correct bottle.

Figure 10:
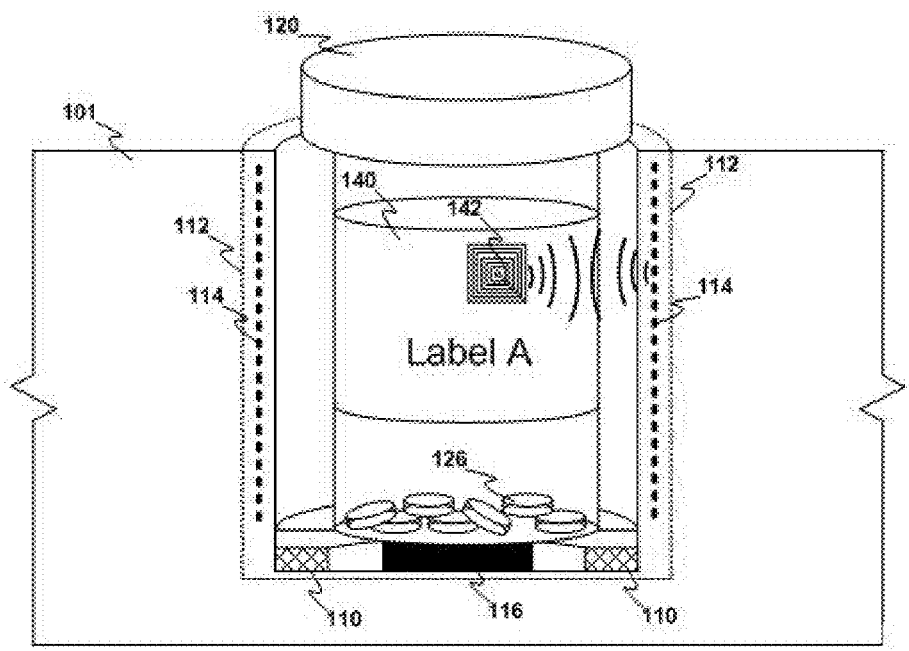
FIG. 10 is a schematic illustrating a receptacle with a RFID reader communicating with an RFID tagged pill bottle, in accordance with one embodiment.

In accordance with an embodiment and illustrated in FIG. 10 is a cross sectional isometric view of a receptacle with a radio frequency identification (RFID) reader. The RFID reader is built into the wall of the receptacle and includes an antenna [114]. The RFID reader antenna [114] picks up the signal from an RFID tag [142] in the label [140] of a pill bottle. A receptacle is surrounded by a faraday cage [112] that helps to block the signal from RFID tags that are in adjacent receptacles. In accordance with an embodiment the RFID tag [142] in a label directly contains all information available for the bottle, including prescription information, medication information, side effect information, and drug interaction information. In accordance with another embodiment the said RFID tag [142] contains a pointer such as a universally unique identifier (UUID) that points to at least one location in at least one database that contains all information available for the bottle.

Figure 11:
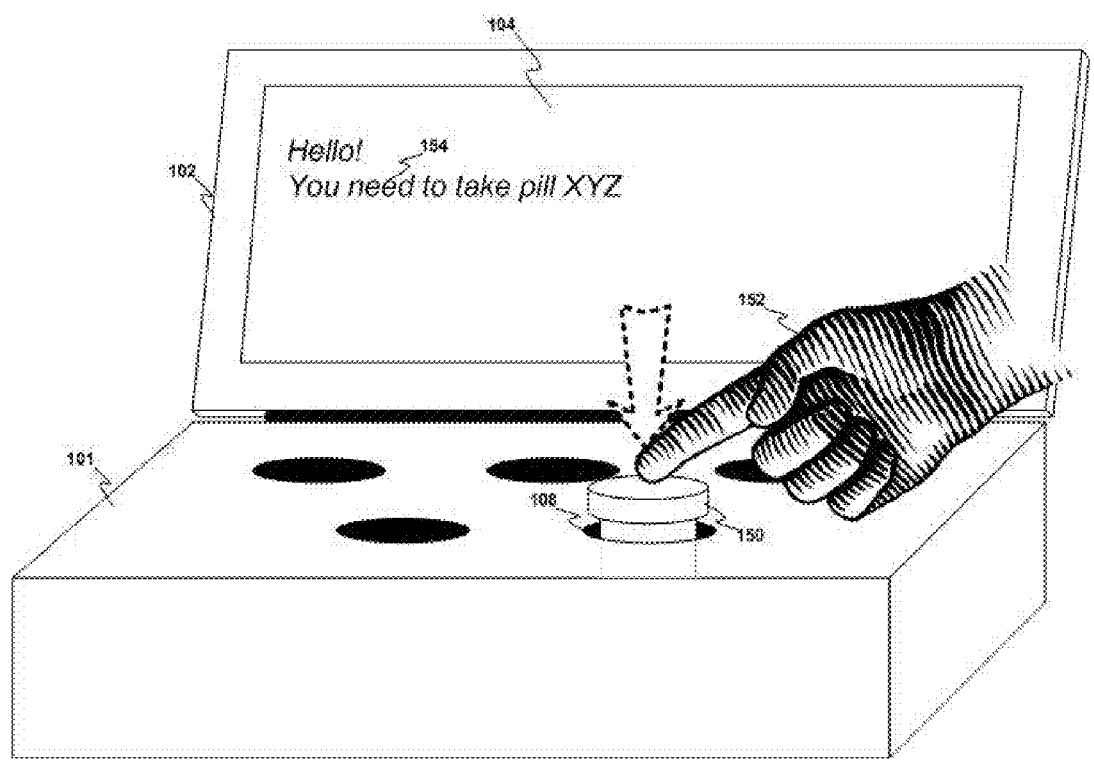
FIG. 11 is an illustration depicting the activation of a feature of an intelligent pill box by depressing a pill bottle with a finger, in accordance with one embodiment.

In accordance with an embodiment and illustrated in FIG. 11 is the activation of an intelligent pill box with an applied pressure. If an intelligent pill box is in a standby mode then applying pressure to a pill bottle [150] in a receptacle [108] will wake the said box into an active mode. The pressure can be applied with a hand [152] by pushing down on the bottle with a finger. In accordance with an embodiment the said pushing of a bottle causes the intelligent pill box device to connect to a network and retrieve information about the medication in said bottle including prescription information. This said information is often provided by a doctor when the medication is prescribed and by a pharmacist at the moment of purchase, but is often forgotten by the user. The said device would offer the service of retrieving this said information from at least one source over a network. The said device would retrieve said information from a variety of sources including a medical industry standard reference that is accessed securely via a public application interface (API). The retrieved information includes prescription information and facts about the medication including the name of the medication, the uses of said medication, the side effects of said medication, drug interactions involving said medication and the like.

In accordance with an embodiment a copy of the prescription information is displayed on the display panel when a user applies pressure to a bottle in a receptacle. This said prescription information can be extracted from an RFID tag using an RFID reader in a receptacle. Said prescription information can also be obtained by an intelligent pill box via communication over a network with a pharmacy or hospital. In accordance with an embodiment the display of the prescription information on the display is a facsimile of the prescription label on the bottle.

Figure 12:
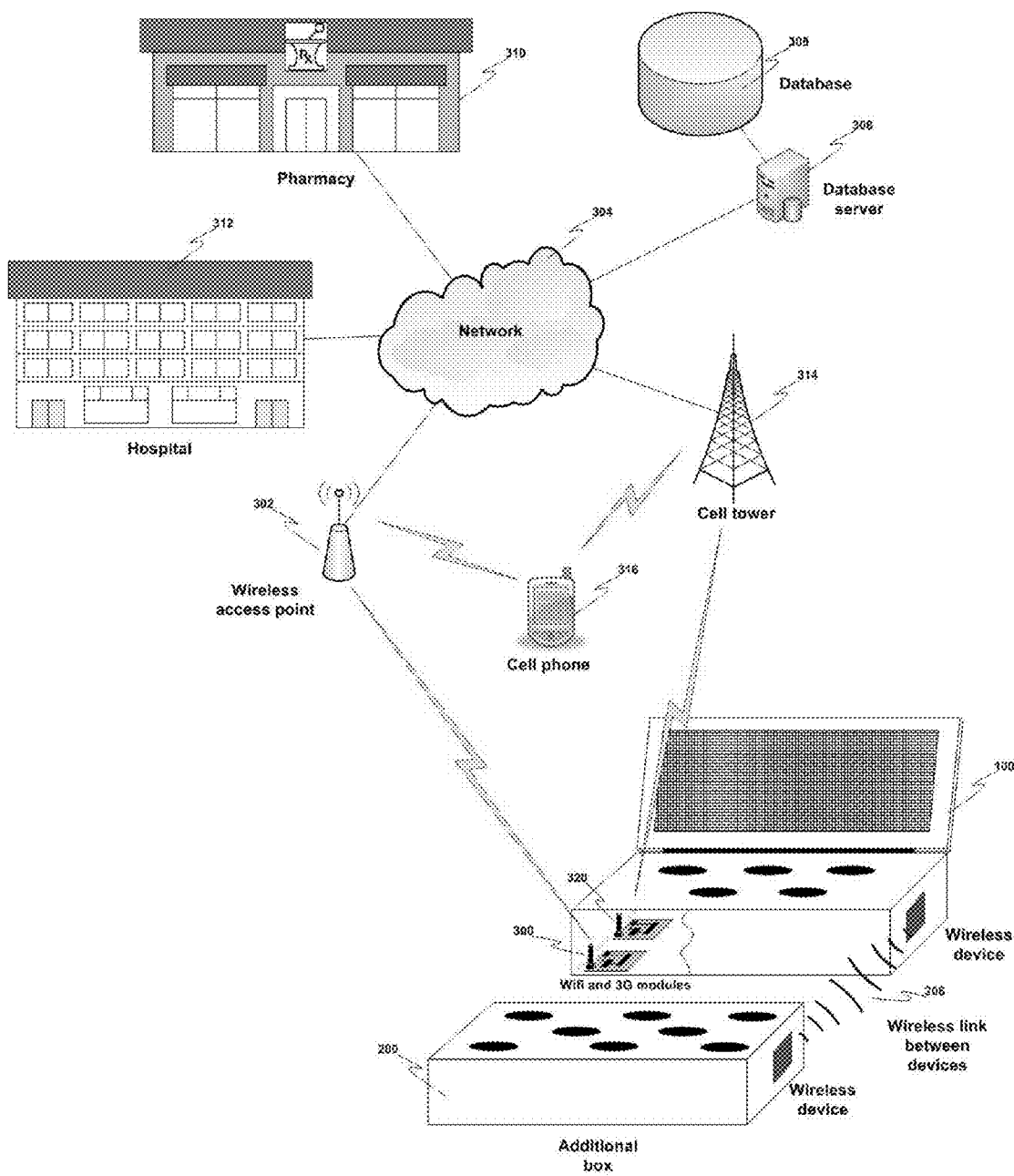
FIG. 12 is a schematic illustrating an intelligent pill box connected wirelessly to a network, in accordance with one embodiment.

In accordance with an embodiment and illustrated in FIG. 12 is a schematic showing an intelligent pill box connected to a network. The intelligent pill box [100] can connect to a network [304], including the world wide web, via a local wireless network or local wireless access point [302]. To connect to the network [304] via a wireless network access point [302] the intelligent pill box [100] has a WiFi module [300]. To connect to the network [304] via a cell phone network, including 3G, the intelligent pill box [100] has a mobile networking device [320]. Via the network [304] the intelligent pill box [100] can access at least one database [308] via a database server [306], and the intelligent pill box [100] can communicate with one or more pharmacies [310] and one or more hospitals [312] and one or more cell phones [316].

Figure 13:
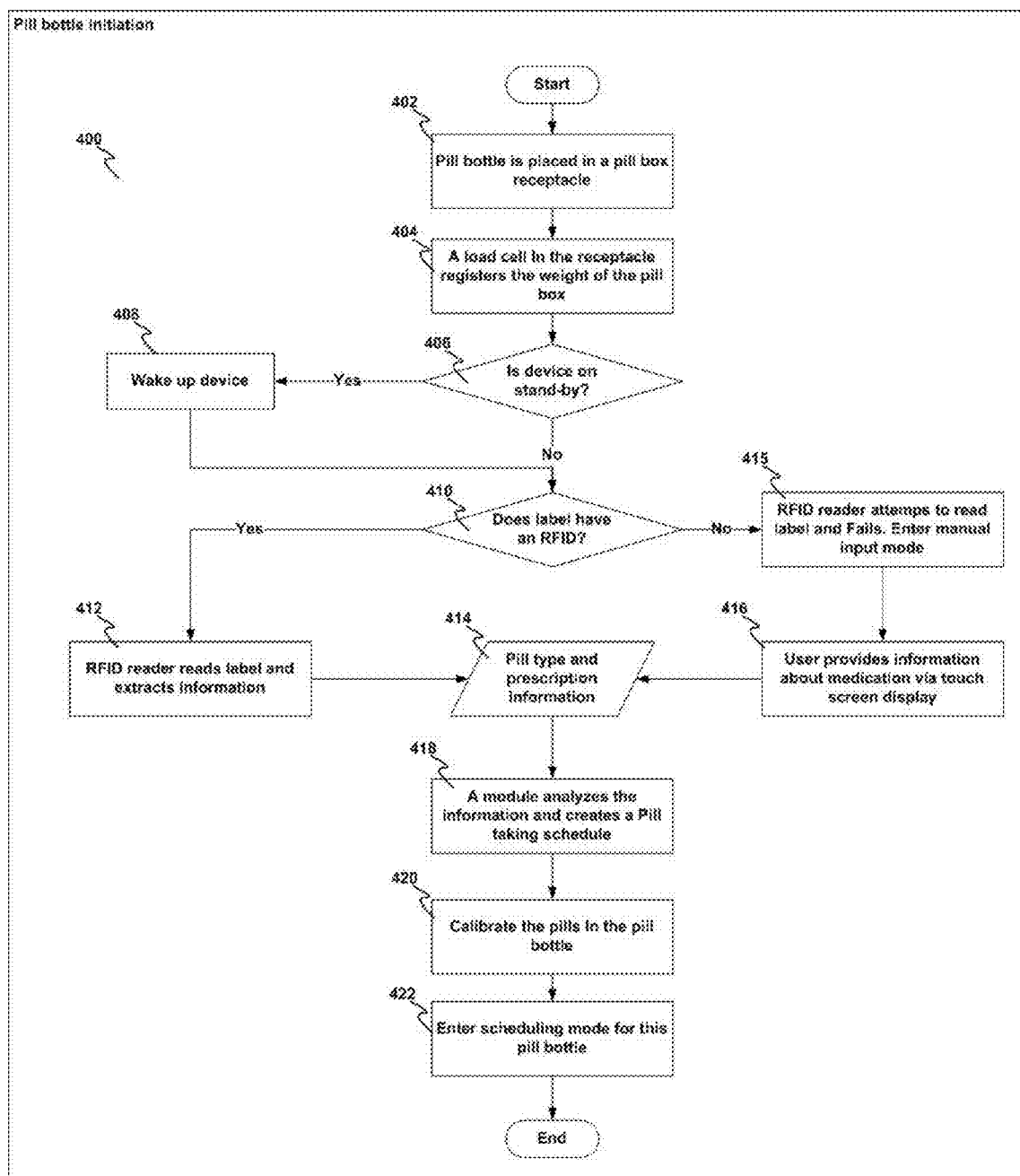
FIG. 13 is a flow chart illustrating steps in the process of pill bottle initiation, in accordance with one embodiment.

In accordance with an embodiment and illustrated in FIG. 13 is a flow chart showing steps for initiating a pill bottle when it is first introduced to an intelligent pill box receptacle. The said initiating is a process of inputting information regarding a pill bottle into the intelligent pill box so that the said intelligent pill box has information on which it can act.

To initiate a pill bottle the said bottle is placed in a pill box receptacle [402] where a load cell in the receptacle registers the weight of the pill box [404]. The change in weight on the load cell signifies to the intelligent pill box device that a pill bottle has been placed in the device. If the device is in a standby mode [406] then the device is made to wake up [408]. If the pill bottle label has a radio frequency identification (RFID) tag then an RFID reader reads the RFID tag and extracts information [412]. The extracted information [414] includes information about the medication within the bottle and information about the prescription associated with the bottle. The medication information can include the name of the medication, the total amount of medication in the bottle, the expiry date of the medication, side effects of the medication, drug interactions, and any other information that would typically be on the label of a pill bottle. The said prescription information includes all information that is provided to the user with regards to taking the medication, including frequency, duration and dosage. If there is no RFID tag in the label then the RFID reader will fail to detect an RFID tag and enter a manual input mode [415]. In a manual input mode a user provides the medication information and the prescription information manually via the touch screen display [416]. A scheduling module analyzes [418] the said prescription information and medication information and creates a pill taking schedule. A calibration module then calibrates the pill bottle [420]. The intelligent pill box then enters the scheduling mode for this pill bottle [422].

Figure 14:
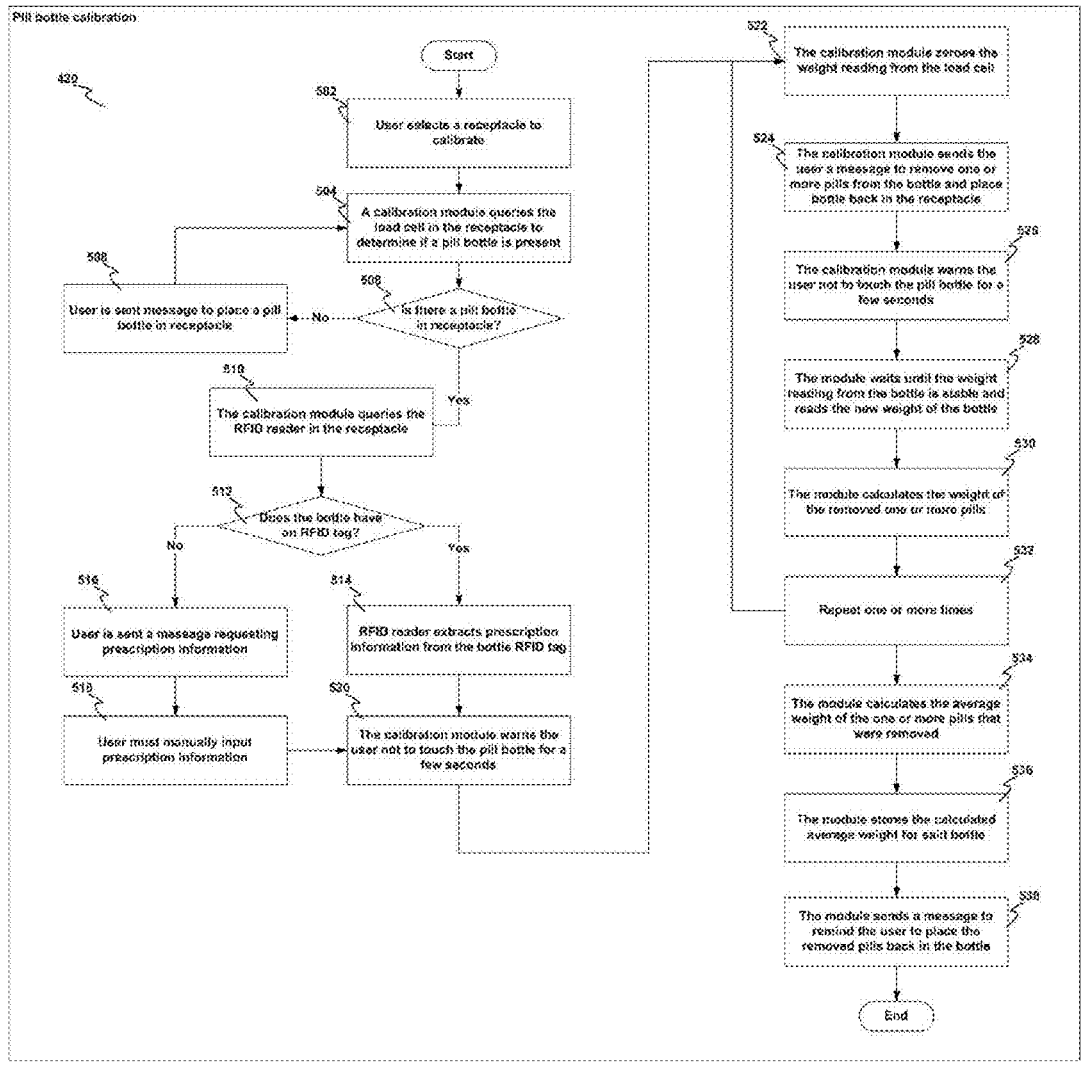
FIG. 14 is a flow chart illustrating steps in the process of pill bottle calibration, in accordance with one embodiment.

In accordance with an embodiment and illustrated in FIG. 14 is a flow chart depicting steps for calibrating a pill bottle using an intelligent pill box. Calibrating a pill bottle includes steps to measure the average weight of a pill within a specific bottle of pills. The said calibration can be done by a calibration module. The calibration is required to determine the average weight of a pill in a bottle placed in a receptacle. This is necessary since there is no standard pill weight for any given medication and since the weight of a pill is not necessarily related to the amount of active medication within said pill. For example, a pill with 100 mg of active medication can weigh the same as a pill with 200 mg of said active medication. The two said pills would have a different amount of filler product. With reference to FIG. 14 the pill bottle calibration [420] begins by selecting [502] a receptacle that contains a pill bottle to be calibrated. The receptacle can be selected via the display panel or by pushing down on a pill bottle within a receptacle to activate the load cell at the bottom of said receptacle. With a receptacle selected, the calibration module queries [504] the load cell in the receptacle to determine if said receptacle contains a pill bottle. If no pill bottle is present then the calibration module sends the user a message [508] to place a pill bottle in said receptacle. If a pill bottle is in the receptacle the calibration module queries [510] the RFID reader in the receptacle. If the bottle does not have an RFID tag then the user is sent a message [516] requesting that the prescription information be input manually [518]. If the bottle has an RFID tag the RFID reader reads the tag and extracts prescription information [514]. Once the calibration module obtains the prescription information the calibration module sends the user a message [520] to not touch the pill bottle for a few seconds. The calibration module then zeroes [522] the weight reading from the load cell. The said zeroing of the weight reading includes the calibration module taking the said reading of the weight value as a base value. It can assign a value of zero to the said base value. The calibration module then sends the user a message [524] to remove one or more pills from the bottle and to place the bottle back in the receptacle without said removed pills. The calibration module then sends the user a message [526] to not touch the pill bottle for a few seconds. The module waits until the weight reading from the bottle is stable and then reads the new weight [528] from the load cell. The module calculates the weight of the removed one or more pills [530]. The calibration module can repeat the measurement [532] for more pills until a requirement for accuracy is met. The module calculates [534] the average weight of the one or more pills that were removed. The module stores the calculated average weight [536] for said bottle in a memory. The module sends a message [538] to remind the user to put the removed pills back in the bottle.

Figure 15:
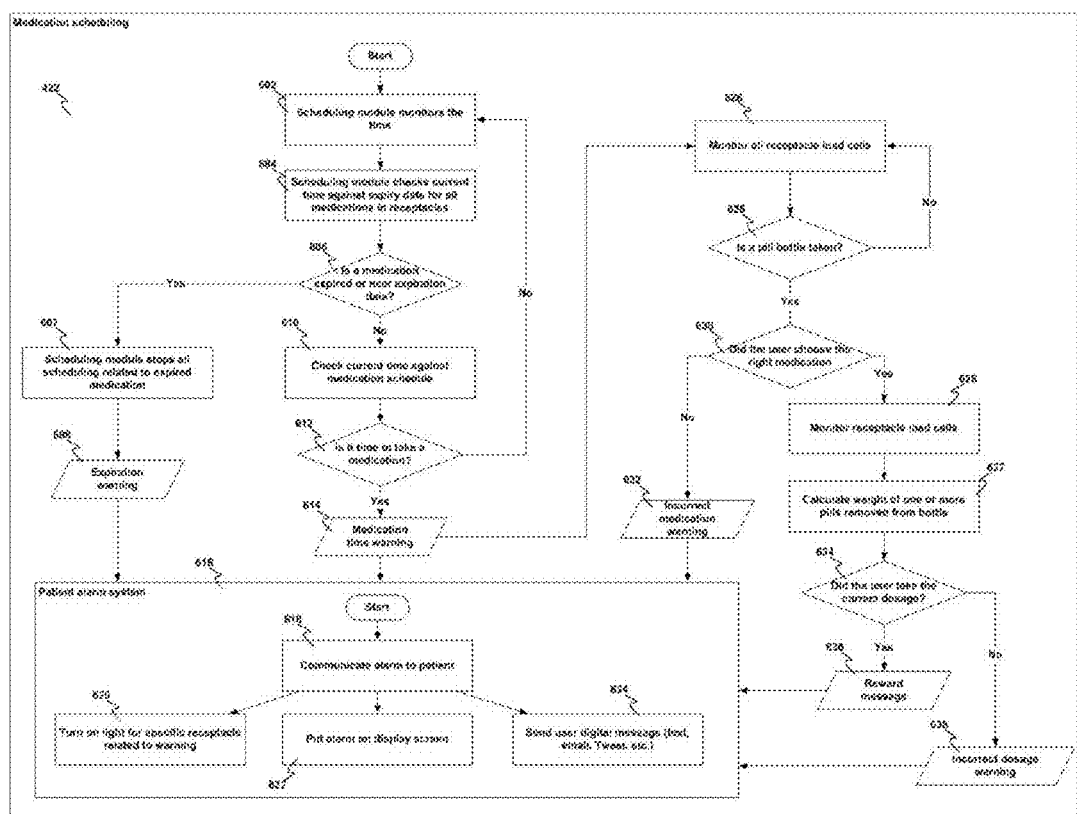
FIG. 15 is a flow chart illustrating steps in the process of medication scheduling, in accordance with one embodiment.

In accordance with an embodiment and illustrated in FIG. 15 is a flow chart of a process for scheduling medication with an intelligent pill box. In order to create a schedule for warning a user to take medication, a scheduling module monitors the time [602]. To avoid dangerous issues with expired medication the scheduling module checks the current time against the expiry date for all medications within receptacles [604]. If a medication is expired or near its expiry date the scheduling module sends an expiration warning [608] to a patient alarm system [616] and stops all scheduling related to the expired medication [607]. If medication is not expired then the current time is checked against the medication schedule [610] to determine if it is time to take a medication [612]. If a medication is due to be taken then a warning message [614] is sent to the patient alarm system [616]. The said warning message [614] includes the medication name, the amount to be taken, the exact time it should be taken, and any special requirements. The scheduling module then monitors [626] all the receptacle load cells. If a pill bottle is removed [628] from a receptacle the load cell of said receptacle will register a large drop in weight. The scheduling module will then determine [630] if the user has chosen the correct medication. If the user chose the wrong medication then an incorrect medication warning message [632] is sent to the patient alarm system [616]. If the user has chosen the correct medication then the scheduling module monitors the load cell values [626] and waits for the user to replace the removed pill bottle in a receptacle. Once the pill bottle is placed back in a receptacle the scheduling module calculates the loss in weight due to the removal of the one or more pills from said bottle [627]. The module determines [634] if the user took the correct amount of pills with respect to the prescription for said bottle. If the user took an incorrect dosage then an incorrect dosage warning message [638] is sent to the patient alarm system [616]. If the correct dosage was taken then a reward message [636] could be sent to the patient alarm system [616].

In accordance with an embodiment there is a patient alarm system [616] that manages the communication of alarms and messages to the user. The said patient alarm system [616] can communicate via the display panel, lights in or around a receptacle, audio speakers and digital messages. If for example the patient alarm system receives a message to warn a user about a medication in a specific receptacle then the said alarm system can use the light in the receptacle [620] to alert the user to the appropriate receptacle. An alarm can also be put on the display screen [622] explaining the alarm to the user. The patient alarm system can also communicate with the user and any other authorized third party via a digital message [624]. The said digital message includes text messages, emails, Tweets and the like. The said third party can include a doctor, a pharmacist, a relative, a hospital.

In accordance with several embodiments a module in an intelligent pill box is constantly monitoring the load cells of all receptacles and reading the RFID tags of all pill bottles. A pill bottle that has been calibrated in a first receptacle can be removed from said receptacle and placed in a second receptacle without needing to be recalibrated. The calibration information created for said bottle in the first receptacle is reassigned to the second receptacle. Similarly, the scheduling information for a pill bottle will stay assigned to said pill bottle regardless of the receptacle said pill bottle is placed in.

In accordance with an embodiment an intelligent pill box device is registered by a user to a service over a network. Said service is provided by a third party that accepts requests for prescriptions, fills said prescriptions and then sends said filled prescriptions by a delivery system to an address. The address is provided by the user to the said third party. As an example said service could be provided by a retail pharmacy with a secure mail order application interface (API) system. Said intelligent pill box which is registered for the service monitors all the medication bottles in all receptacles and uses at least the load cell information from said receptacles to determine the amount of medication remaining in said bottles. When a medication within a receptacle reaches a threshold then said intelligent pill box communicates with said service over a network and sends a request to refill said medication. The threshold can be based on the number of pills remaining in a bottle. For example a threshold can be set for a bottle that has less than 10 pills. The said threshold can also be based on the estimated amount of time remaining before a bottle is empty. The intelligent pill box uses the rate of pill taking and the amount of pills remaining in a bottle to calculate an estimate of the amount of time remaining before said bottle becomes empty. The said rate of pill taking is determined from prescription information which includes the dosage and frequency for the medication. The amount of pills remaining in a bottle is estimated from load cell information and the calibration data for said bottle. The load cell information is used to calculate the weight of said bottle with pills and the calibration data defines the weight of a single pill. Subtracting the weight of the bottle without pills from the weight of the bottle with pills results in an estimate of the weight of the pills. Dividing said weight of the pills by the weight of a single pill results in an estimate of the number of pills remaining in said bottle.

In accordance with an embodiment said time threshold can be linked to an average amount of delivery time required by said service. For example said service might require prescription requests to be sent 96 hours before delivery. Said service might require that said request include a credit card number as well as identification information for the user requesting medication. Said identification information can including insurance numbers. In accordance with an embodiment when a threshold is reached the intelligent pill box displays a message on the display that informs the user that a request for more medication is about to be made to said service. The user would have the option to approve, cancel and delay the order. In accordance with an embodiment the user could program the intelligent pill box to automatically send the request for a refill to said service without waiting for approval from the user.

In accordance with an embodiment the intelligent pill box device monitors all medication placed within receptacles, determines adverse reactions from mixtures of said medicines and provides a warning. Some users may get prescriptions from different doctors and may purchase medications from different pharmacies. As a result, said medications might be incompatible and may result in an adverse drug event via their interaction. The said intelligent pill box verifies all interactions from the combinations of the medications within all receptacles. To determine any interactions between medication the said intelligent pill box sends secure and anonymous information to an industry-standard reference service or database that is accessible via a public application interface (API). In accordance with one embodiment the service would compute the interaction potential between medications and return appropriate warning messages regarding dangerous interactions to the device. In accordance with another embodiment the service returns information on each medication and the intelligent pill box determines possible interactions and generates appropriate warning messages. Any warning messages are displayed to the user via the said patient alarm system that includes using the display panel, audio system, digital messages and receptacle lighting system. In accordance with an embodiment the intelligent pill box prompts a user to consult a doctor to verify that an interaction generating a warning is known and deemed therapeutically acceptable. If the interaction is deemed acceptable, the user can record this fact in the device so that said device no longer warns the user of the potential negative interaction. If the user does not take action to ensure the safety of the interaction the warning will persist until the user takes action. In accordance with another embodiment the intelligent pill box directly contacts an authorized third party to warn them of the potential negative interaction. Said authorized third party would be authorized by the user of the device and can include one or more doctors, one or more pharmacists, one or more family members, one or more friends, and the like.

In accordance with an embodiment the intelligent pill box device records all user interaction with the medication within said device including all user interaction with any additional intelligent pill box devices. The device monitors user patterns regarding the taking of medication and creates a report of said patterns. The user can choose not to have the device monitor medication taking. Said report can be shared with third parties over a network whereby said third parties are authorized by the user of the device. Said third parties can include doctors, pharmacies, hospitals, insurance companies and public health departments. The said report can be useful for a doctor to monitor the compliance of a patient with respect to a prescription. The said report can be useful for user compliance with medication therapy management programs. The information within said reports can also be valuable information for insurance companies and government agencies with respect to public health and associated costs. The information within said reports can be shared with third party organizations in an anonymous way. The anonymization of healthcare data is a standardized process that obeys to the rules of the Health Insurance Portability and Accountability Act of 1996 (HIPAA). HIPAA-compliant data contains all of the useful clinical information except any information that can be used to reconstruct the identity of the patient who provided said data.

In accordance with an embodiment there is provided a method for rewarding users for compliance with a prescription. The method can include linking a consumer benefits and rewards program to the level of compliance a user has towards taking their medication and it can include tracking behavioral compliance and assigning reward points for prescribed behaviors. The method comprises using an intelligent pill box to record information every time a user takes one or more pills from a bottle in a receptacle in said box. Said bottle having an associated prescription. Said recorded information includes the name of the pills taken, the number of pills taken, and the time when said one or more pills are taken. In an aspect of the method said recorded information is collected and sent over a network to a third party along with said prescription information. Credit card information as well as identification information for the participating user can be sent as well. The third party receives said information and compares the recorded information with the prescription information to determine the amount of compliance between said user's actions and said prescription. If the user reaches a threshold of compliance then said third party offers one or more rewards to said user. A reward can include a discount on future purchases of medication, access to streaming coupons, points for a point system, offers for discounted or highly targeted/customized retail goods and services and the like. A user might be required to register to receive said rewards and benefits. A user could opt-in or opt-out of said program. A user could also provide ratings to increase or diminish certain types of offers based on the personal interest of said user. Said third party might require the user to register product interests to organize reward options.

In accordance with another embodiment the intelligent pill box compares the recorded information with the prescription information to determine the amount of compliance between said user's actions and said prescription and then transmits the level of compliance to said third party.

In accordance with an embodiment the threshold is reached the intelligent pill box displays a message on the display that informs the user that they have qualified to redeem points for retail goods or services. The user would have the option to approve, cancel and delay the goods or services.

Figure 16:
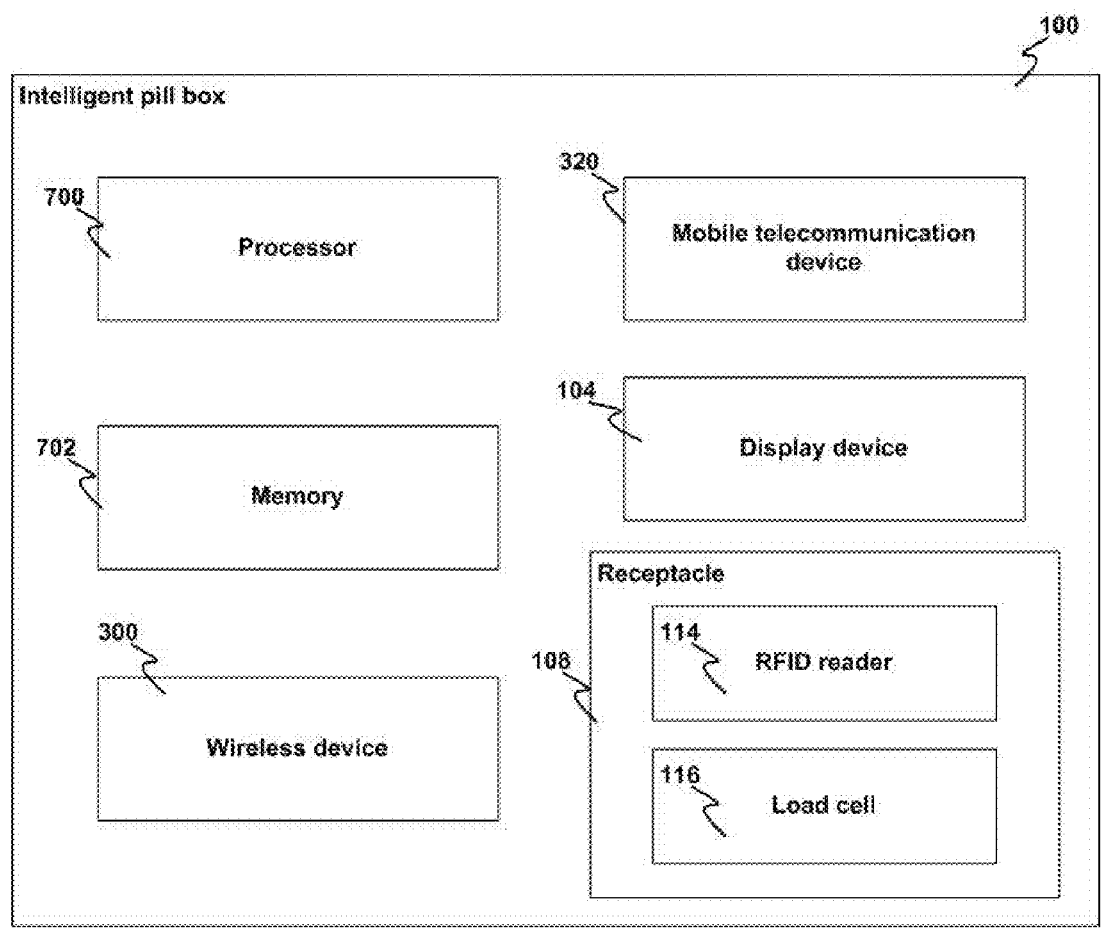
FIG. 16 is s schematic illustrating components in an intelligent pill box, in accordance with an embodiment.

In accordance with an embodiment FIG. 16 illustrates an intelligent pill box device. The device [100] includes a processing device [700], a memory [702], a wireless device [300], a mobile telecommunication device [320], and a display device [104]. The processing device [700] is any type of processor, processor assembly comprising multiple processing elements (not shown), having access to a memory [702] to retrieve instructions stored thereon, and execute such instructions. Upon execution of such instructions, the instructions implement the processing device [700] to perform a series of tasks as described throughout the text above and in the Figures. The memory 106 can be any time of memory device, such as random access memory, read only or rewritable memory, internal processor caches, and the like. The processing device [700] also communicates with one or more RFID readers [114] and one or more load cells [116] within one or more receptacles [108].

While illustrated in the block diagrams as groups of discrete components communicating with each other via distinct data signal connections, it will be understood by those skilled in the art that the embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment.

It should be noted that the present invention can be carried out as a method, can be embodied in a system, a computer readable medium or an electrical or electro-magnetic signal. While specific embodiments have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. An intelligent pill box device, comprising:
a base and a display panel;
said base including a plurality of cylindrical shaped receptacles for storing medication bottles, each receptacle including a radio frequency identification reader, and each receptacle surrounded by a faraday cage, and each receptacle containing a load cell at the bottom of the receptacle to measure the weight of the contents of the receptacle;
said base including a processing device and a memory, said processing device executing at least:
instructions relating to weighing medication in a medication bottle that is placed in the receptacle, instructions relating to using said reader to extract information from a radio frequency tag on said medication bottle instructions relating to using at least said extracted information to determine a medication schedule for taking said medication and notifying a user when it is time to take said medication, and instructions relating to monitoring compliance with said medication schedule;
said display panel attached to the base with a hinge, and said display panel including a flat screen display to display information to a user;
said base including a wireless device for connecting to a wireless network wherein said intelligent pill box device communicates with a third party service provider via another network that is connected to said wireless network, and
wherein said user has a rewards account with said third party and said intelligent pill box device is registered to said rewards account, and wherein said third party service provider provides said user with a reward to said rewards account if the user complies with said medication schedule based on information communicated from said intelligent pill box to said third party via said wireless network;
using a calibration process and the load cell to determine the average weight of individual medication within the medication bottle;
alerting a user to take one or more of said medication according to the medication schedule;
determining whether said user took the medication according to said medication schedule by using the total weight of the medication bottle and the medication before and after the alert and calculating whether the correct amount of medication was removed from the medication bottle based on the average weight of each individual medication;
transmitting a confirmation that the user complied with the medication schedule from the intelligent pill box device to the third party via the wireless network; and
having the third party provide the user with a reward to the rewards account in response to the received confirmation;
wherein the process further comprises alerting the user that additional medication should be ordered based on based on:
(i) the average time for delivering the additional medication from the third party to the user and
(ii) the amount of medication left in the medication bottle.

2. The device of claim 1, wherein each receptacle includes at least one light, the light controlled by the processing device and used to direct users to a specific receptacle.

3. The device of claim 1, wherein said display panel is detachable from the base.

4. The device of claim 1, wherein each cylindrical shaped receptacle is 2 inches in diameter.

5. The device of claim 1, wherein said base includes a wireless device for communicating wirelessly with another intelligent pill box device.

6. The device of claim 1, wherein said wireless device includes a mobile telecommunications technology device and said wireless network is a mobile phone network.

7. A medication assistance method, comprising:
providing an intelligent pill box device, comprising:
a base and a display panel;
said base including a plurality of cylindrical shaped receptacles for storing medication bottles, each receptacle including a radio frequency identification reader, and each receptacle surrounded by a faraday cage, and each receptacle containing a load cell at the bottom of the receptacle to measure the weight of the contents of the receptacle;
said base including a processing device and a memory, said processing device executing at least:
instructions relating to weighing medication contained in a medication bottle that is placed in the receptacle, instructions relating to using said reader to extract information from a radio frequency identification tag on said medication bottle, instructions relating to using at least said extracted information to determine a medication schedule for taking said medication and notifying a user when it is time to take said medication, and instructions relating to monitoring compliance with said medication schedule;
said display panel attached to the base with a hinge, and said display panel including a flat screen display to display information to a user; and
said base including a wireless device for connecting to a wireless network wherein said intelligent pill box device communicates with a third party service provider via another network that is connected to said wireless network, and wherein said user has a rewards account with said third party and said intelligent pill box device is registered to said rewards account;
using the radio frequency identification reader to extract information from the radio frequency identification tag on the medication bottle;
using the extracted information from the radio frequency identification tag to determine the medication schedule for taking the medication;
using the load cell to determine the total weight of the medication bottle and the medication;
using a calibration process and the load cell to determine the average weight of individual medication within the medication bottle;
alerting a user to take one or more of said medication according to the medication schedule;
determining whether said user took the medication according to said medication schedule by using the total weight of the medication bottle and the medication before and after the alert and calculating whether the correct amount of medication was removed from the medication bottle based on the average weight of each individual medication;
transmitting a confirmation that the user complied with the medication schedule from the intelligent pill box device to the third party via the wireless network; and
having the third party provide the user with a reward to the rewards account in response to the received confirmation;
wherein the process further comprises alerting the user that additional medication should be ordered based on based on:
(i) the average time for delivering the additional medication from the third party to the user and
(ii) the amount of medication left in the medication bottle.

8. The method of claim 7, wherein said medication schedule comprises at least: a list of times for taking said pills; and the number of pills to take at each time on said list.

9. The method of claim 7, wherein said intelligent pill box records all interactions of a user with said intelligent pill box and transmits said information via said wireless network to said third party.

10. The method of claim 7, wherein said wireless device includes a mobile telecommunications technology device and said wireless network is a mobile phone network.

11. The method of claim 7, wherein the process further comprises displaying a reward message to the user after determining that the user complied with the medication schedule.

* * * * *